(12) United States Patent
Wogoman

(10) Patent No.: US 7,544,277 B2
(45) Date of Patent: Jun. 9, 2009

(54) ELECTROCHEMICAL TEST SENSORS

(75) Inventor: Frank W. Wogoman, Granger, IN (US)

(73) Assignee: Bayer Healthcare, LLC, Tarrytown, NY (US)

( * ) Notice: Subject to any disclaimer, the term of this patent is extended or adjusted under 35 U.S.C. 154(b) by 809 days.

(21) Appl. No.: 10/846,779

(22) Filed: May 17, 2004

(65) Prior Publication Data

US 2004/0253367 A1 Dec. 16, 2004

Related U.S. Application Data

(60) Provisional application No. 60/477,739, filed on Jun. 12, 2003.

(51) Int. Cl.
C25B 9/00 (2006.01)
C25B 9/06 (2006.01)
C25B 11/02 (2006.01)

(52) U.S. Cl. .................. 204/400; 204/288; 204/279; 204/271; 204/193; 204/194; 204/403.14; 204/242; 204/403.02

(58) Field of Classification Search ............... 427/58; 204/434, 400, 288.1, 280, 409, 777.5, 272, 204/271, 278.5, 403.01–403.15, 416–418, 204/431, 288, 279, 242, 193, 194
See application file for complete search history.

(56) References Cited

U.S. PATENT DOCUMENTS 4,413,407 A 11/1983 Columbus
4,761,381 A 8/1988 Blatt
5,437,999 A * 8/1995 Diebold et al. .......... 204/403.11
RE36,268 E * 8/1999 Szuminsky et al. ...... 205/777.5
6,156,173 A * 12/2000 Gotoh et al. ........... 204/403.04
6,258,229 B1 7/2001 Winarta
6,416,641 B1 7/2002 Ikeda et al. ................. 204/403
2002/0092615 A1* 7/2002 Iida ....................... 156/345.31

FOREIGN PATENT DOCUMENTS

WO WO 98/43073 * 10/1998

OTHER PUBLICATIONS

Japanese Patent Abstract (Translated), S64-044842 A, by KINYA, Published Feb. 1989.*
O'Shea, Thomas J. and Lunte, Susan M., "Capillary Electrophoresis/Electrochemistry," Current Separations 14:1, 1995, pp. 18-23.
European Search Report corresponding to European Patent Application Serial No. 0401288.1, dated Jul. 28, 2004, 4 pages.

* cited by examiner

Primary Examiner—Alex Noguerola
Assistant Examiner—J. Christopher Ball
(74) Attorney, Agent, or Firm—Nixon Peabody LLP

(57) ABSTRACT

Sensors for the electro-chemical analysis of samples and methods for the manufacturing of sensors allow for more efficient manufacture and use of electro-chemical sensors. Flexible sheets, such as polycarbonate sheets, are used to easily manufacture sensor components, with sensor chemistry being applied to the sensor components at manufacture. Sensors may be manufactured with modular components, enabling easy production-line manufacture and construction of electro-chemical sensors with significant cost savings and increased efficiency over existing sensor styles and sensor manufacturing techniques.

17 Claims, 3 Drawing Sheets

ELECTROCHEMICAL TEST SENSORS

CROSS-REFERENCE TO RELATED APPLICATION

This application claims benefit to U.S. Provisional Application No. 60/477,739, which was filed on Jun. 12, 2003

FIELD OF THE INVENTION

The present invention relates generally to electro-chemical analysis and more specifically to a diagnostic sensor for fluid analysis.

BACKGROUND OF THE INVENTION

Electro-chemical analysis is one technique available for the analysis of both charged and neutral molecules. Such analysis is generally very fast, requires small volumes of samples and reagents, and costs much less than other analysis techniques. Electro-chemical analysis can be used for a wide range of applications, including testing of bodily fluids, such as glucose testing of blood samples. Electro-chemical detectors do not require an optical carrier, and as a result they are much less costly than absorption and fluorescence detectors. Electro-chemical analysis systems can test samples which are collected via capillary action within a sensor.

Generally, most capillary-filled sensors are produced by a methodology wherein active chemical areas are captured within a molded capture area. This assembly process requires precision molding, and may require very precise printing of reagents and other chemicals in very small areas. Further, the use of a formed molded or laminated structure to define and produce a capillary channel results in a sample being substantially enclosed by formed walls. Irregularities in walls may frictionally hinder sample flow and variations of the walls in different sensors may result in sample fill variations. The resulting sample fill variations affect the test results and decrease the overall accuracy of the analysis. Further, the possibility of trapping air bubbles may be increased with existing sensors and sensor construction methods. There is a need for electro-chemical sensors and sensor construction methods which reduce or eliminate these problems to increase the efficiency and accuracy of electro-chemical sample analysis.

SUMMARY OF THE INVENTION

According to one embodiment of the present invention, an electro-chemical sensor consists of a flexible substrate with a chemical strip uniformly provided thereon.

According to another embodiment of the present invention, an electro-chemical sensor is provided wherein the size and form of electrode areas are defined by precision punching. The sample area of the electro-chemical sensor is formed by the overlap of two similarly-shaped sheets forming a top and bottom, leaving the sample area open on all sides to form a capillary channel for acquiring samples.

According to another embodiment of the present invention, an electro-chemical sensor is provided wherein the capillary channel is formed by folding an outer sheet over the end of an inner sheet.

According to yet another embodiment of the present invention, an electro-chemical sensor is provided wherein the working and reference electrodes are produced by the same manufacturing operation.

According to still another embodiment of the present invention, linear ribbon processing is used to manufacture electrodes and capillary areas.

According to still another embodiment of the present invention, electro-chemical sensors are produced in a punch and laminate process using relatively low-cost, high-speed equipment.

DETAILED DESCRIPTION OF THE ILLUSTRATED EMBODIMENTS

The present invention is generally directed to electro-chemical sensors and electro-chemical sensor manufacturing methods. Sensors according to the present invention may be used in a variety of settings; one example is use as a glucose testing sensor.

Figure 1:
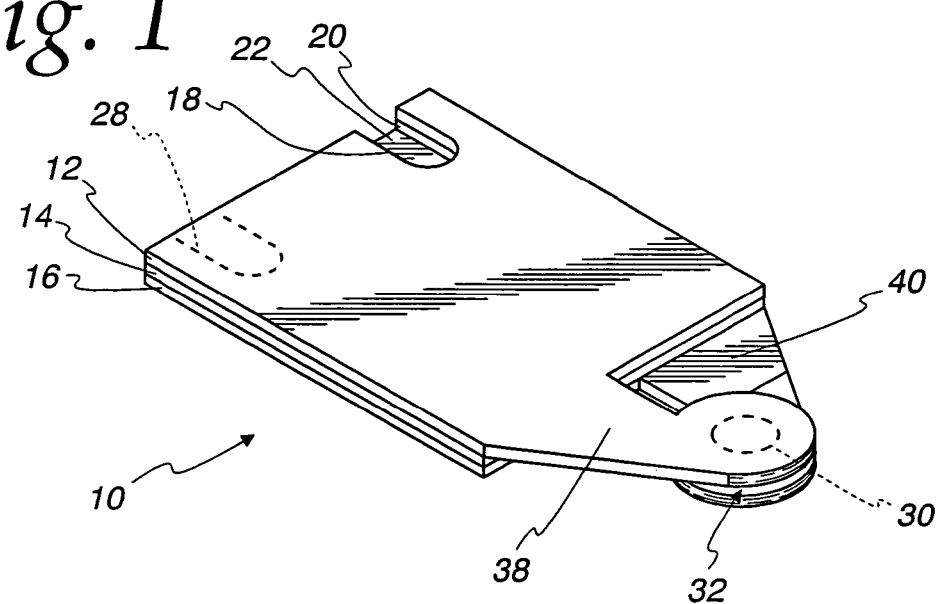
FIG. 1 is a perspective view of an electro-chemical sensor according to one embodiment of the present invention.

FIG. 1 shows an electro-chemical sensor 10 according to one embodiment of the present invention. The electro-chemical sensor 10 comprises a top sheet 12, a spacer sheet 14, and a bottom sheet 16. According to one embodiment of the present invention, the sheets used to construct the sensor 10 are polycarbonate sheets, but other materials may be used in other specific embodiments. According to the embodiment shown in FIG. 1, the top sheet 12 and the bottom sheet 16 of the sensor 10 are identically shaped sheets, inverted and overlapped with the spacer sheet 14 placed between them. Adhesive supplied along the top and bottom of the spacer sheet 14 may be used to secure the top sheet 12 and the bottom sheet 16 to the spacer sheet 14, or other connection means may be used as will be appreciated by those skilled in the art.

The top sheet 12 is provided with a top sheet notch 18 which aligns with a first spacer sheet notch 20 to expose a bottom sheet electrode 22. Similarly, the bottom sheet 16 is provided with a bottom sheet notch 24 which aligns with a second spacer sheet notch 26 (both shown in FIG. 4) to expose a top sheet electrode 28. The electrodes of the embodiment shown in FIG. 1 may merely be exposed areas of the construction material or a coating material on each of the top sheet 12 and the bottom sheet 16, and serve as electrical contacts when the sensor 10 is connected to or inserted into a reading device.

Figure 3:
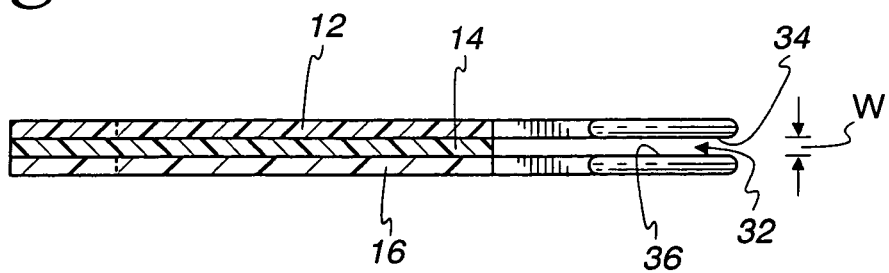
FIG. 3 is a side view of an electro-chemical sensor according to one embodiment of the present invention.

The electrodes interact with a reading device to allow the analysis of a sample 30 collected in a sample fill area 32. The sample fill area 32 is between a top sample contact surface 34 and a bottom sample contact surface 36, as shown in FIG. 3. In the embodiment shown in FIG. 1, the top sample contact surface 34 is integrally formed with the top sheet 12 and is connected to the body of the top sheet 12 by a top neck 38. Similarly, the bottom sample contact surface 36 is integrally formed with the bottom sheet 16 and is connected to the body of the bottom sheet 16 by a bottom neck 40. The overlapping of the top sample contact surface 34 and the bottom sample contact surface 36 combined with the gap provided by the spacer sheet 14 causes a fluid sample 30 to be pulled into and remain within the sample fill area 32 due to capillary action.

Figure 2:
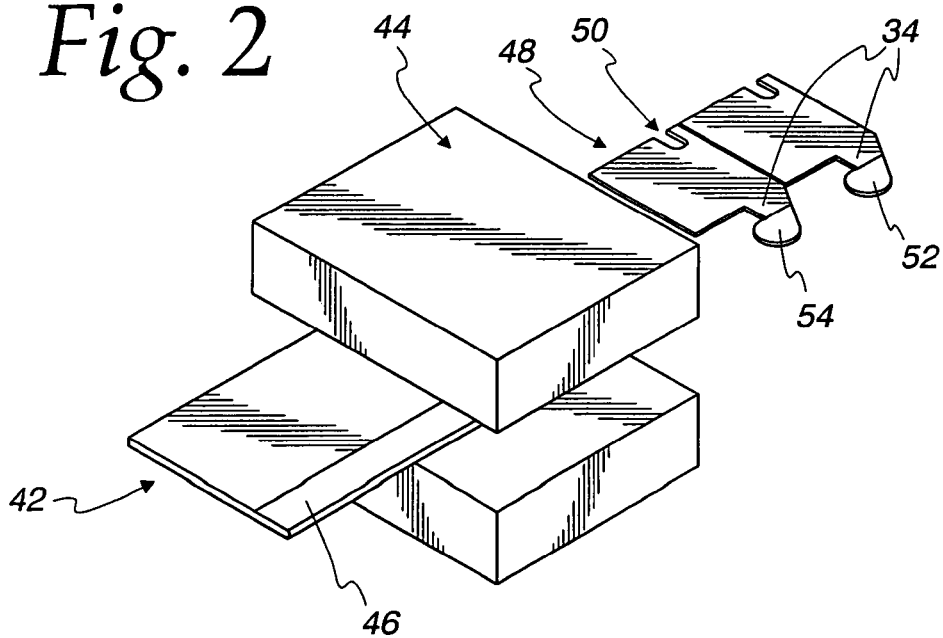
FIG. 2 is a perspective view of sensor component production according to one embodiment of the present invention.

Turning now to FIG. 2, the construction of sensor sheets according to one embodiment of the present invention is shown. A ribbon 42 of construction material is fed into a press 44. According to one embodiment of the present invention, a coating material 46 is provided on the ribbon 42 before the ribbon enters the press 44. The coating material 46 may be a surfactant material for increasing the spread of a sample as it enters the sample fill area 32, a reagent chemical or combination of chemicals with which a sample interacts, or a combination of these.

The press 44 cuts the ribbon material 42 into a series of stock sheets 48. Each stock sheet 48 may be used as a top sheet 12 or a bottom sheet 16 in the construction of a sensor 10 as shown in FIG. 1. Whether the stock sheets 48 are to be used as top sheets or bottom sheets of a sensor may be made dependent upon the coating material 46. According to one embodiment of the present invention, the same coating material is provided on stock sheets 48 to be used as top as on stock sheets to be used as bottom sheets. According to another embodiment, coating material is provided only on the top sheet or only on the bottom sheet. Further, different coating materials may be used on the two sheets.

As shown in FIG. 2, the press 44 punches the ribbon material 42 such that each stock sheet is provided with a stock sheet notch 50, a stock sheet neck 52, and a stock sheet sample contacting surfacee 54. Thus, in the embodiment shown in FIG. 1, a first stock sheet has been inverted above a second stock sheet, thereby forming a top sheet 12 and a bottom sheet 16.

Turning now to FIG. 3, a side view of an electro-chemical sensor 10 is shown, illustrating the structure of one embodiment of the sample fill area 32. The sample fill area 32 is located between the top sample contact surface 34 and the bottom sample contact surface 36, either or both of which may be coated with coating materials. According to one embodiment of the present invention, the open space around the sample fill area 32 eliminates the need for an air vent and substantially eliminates the trapping of air within the sample fill area 32. The volume of the sample fill area 32 is defined by the surface area of the top and bottom sample contact surfaces 34 and 36 and by the separation distance, w, shown in FIG. 3.

According to one embodiment of the present invention, the separation distance w is approximately 0.127 millimeter (0.005 inch), though separations of from approximately 0.0762 millimeter (0.003 inch) to approximately 0.254 millimeter (0.010 inch) may be useful in certain embodiments, and wider or narrower separations may be useful in some embodiments. The separation distance w may be adjusted by varying the width of the spacer sheet 14.

Figure 4:
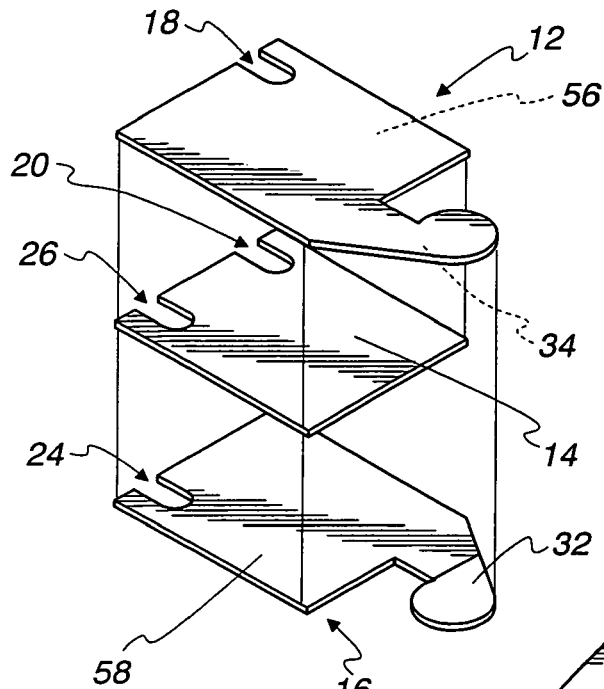
FIG. 4 is an exploded perspective view of an electro-chemical sensor according to on embodiment of the present invention.
Figure 5:
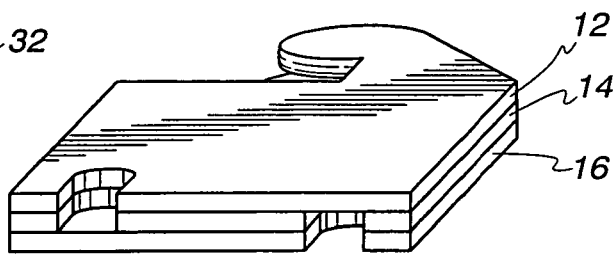
FIG. 5 is an isometric rear view of an electro-chemical sensor according to one embodiment of the present invention.

Turning now to FIGS. 4 and 5, an electro-chemical sensor 10 is shown in an exploded view and an a rear view to more clearly illustrate the construction of a sensor according to one embodiment of the present invention. As shown in FIG. 4, the spacer sheet 14 is provided with first and second spacer sheet notches 20 and 26. In the embodiment shown in FIG. 4, the first spacer sheet notch 20 aligns with a top sheet notch 18 and the second spacer sheet notch 26 aligns with a bottom sheet notch 24. As a result, when the sensor 10 is formed, the alignment of the top sheet notch 18 and the first spacer sheet notch 20 exposes a bottom sheet electrode 22, as shown in FIG. 1. Likewise, the alignment of the bottom sheet notch 24 and the second spacer sheet notch 26 exposes a top sheet electrode 28, as shown in FIG. 1.

According to one embodiment of the present invention, the bottom surface 56 of the top sheet 12 and the top surface 58 of the bottom sheet 16 are coated with conductive material. Thus, electro-chemical analysis of the sample 30 can be performed by connecting the exposed electrodes to an analysis device. According to one embodiment of the present invention, carbon coating is used to enable the bottom surface 56 of the top sheet and the top surface 58 of the bottom sheet to conduct electricity, though other coatings such may be used in certain embodiments of the present invention. The alignment of the notches in the top sheet 12, the spacer sheet 14, and bottom sheet 16 is further illustrated in FIG. 5, which shows a rear view of a sensor 10 according to one embodiment of the present invention.

Some embodiments of the present invention thus allow for the size and form of stock sheets 48 to be defined by precision punching, or another precise method of production, allowing both a top sheet 12 and a bottom sheet 16 to be formed from the same or a very similar process. Further, the application of conductive components, reagents, surfactants, or other chemicals is facilitated by the fact that the components may be applied uniformly over an entire ribbon 42 of construction material or in a single band of coating material 46, reducing or eliminating the need for precision printing or other precision placement of coating materials.

Figure 6:
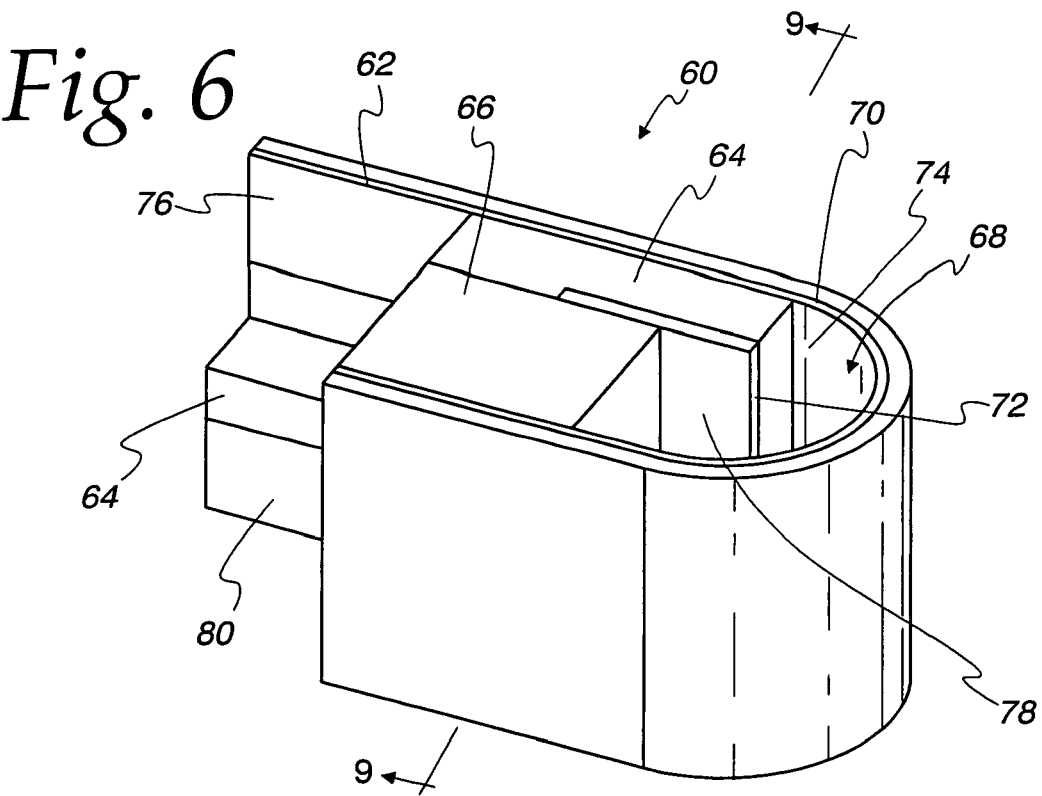
FIG. 6 is a perspective view of an electro-chemical sensor according to one embodiment of the present invention.

Turning now to FIG. 6, a sensor 60 according to an alternative embodiment of the present invention is shown. In a sensor 60 according to the embodiment shown in FIG. 6, an outer sensor sheet 62 is at least partially wrapped around an inner sensor sheet 64. A spacer sheet 66 separates the outer sensor sheet 62 from the inner sensor sheet 64 and provides for a sample fill area 68. According to one embodiment of the sensor 60, the outer sensor sheet 62, the inner sensor sheet 64, and the spacer sheet 66 are comprised of polycarbonate, though other materials such as polypropylene may be used in the construction of the sheets.

Figure 7:
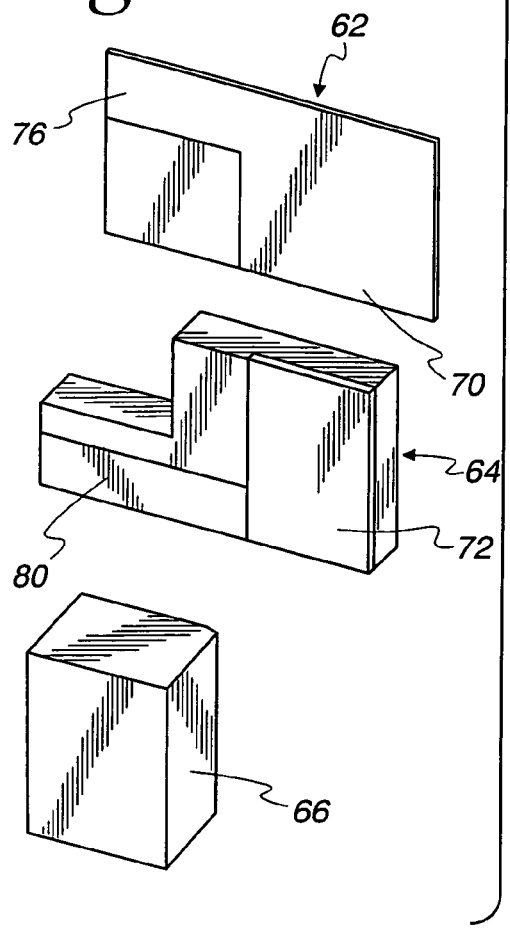
FIG. 7 is an exploded perspective view of an electro-chemical sensor according to on embodiment of the present invention.

An outer electrode area 70 is positioned on the inner surface of the outer sensor sheet 62, and an inner electrode area 72 is positioned on a surface of the inner sensor sheet 64. As shown in FIG. 7, the outer electrode area 70 is provided in a generally "L" shaped layer on the outer sensor sheet 62. Likewise, the inner electrode area 72 is provided in a generally "L" shaped layer on the inner sensor sheet 64. According to the embodiment shown in FIGS. 6 and 7, the spacer sheet 66 is not provided with an electrode area.

As shown in FIG. 6, the outer electrode area 70 a single electrode coating, functionally divided between an outer electrode sample area 74 and an outer electrode contact area 76.

Similarly, the inner electrode area 72 is functionally divided between an inner electrode sample area 78 and an inner electrode contact area 80. The electrode sample areas contact a sample when the sample fill area 68 is filled with a sample, and conduct electricity to the electrode contact areas, which may be connected to an analysis device to allow electro-chemical analysis of a sample within the sample fill area 68.

According to one embodiment of the present invention the outer electrode area 70 is a reference electrode and the inner electrode area 72 is a working electrode. According to another embodiment of the present invention, the outer electrode area 70 may be the working electrode and the inner electrode area 72 may be the reference electrode. The reference electrode may be a printed carbon electrode, or another type of electrode. The working electrode may be a printed carbon electrode with a reagent placed thereon. According to one embodiment of the present invention, the entire working electrode is a printed carbon electrode, with reagent placed only on the part of the electrode that will contact a sample.

Figure 8:
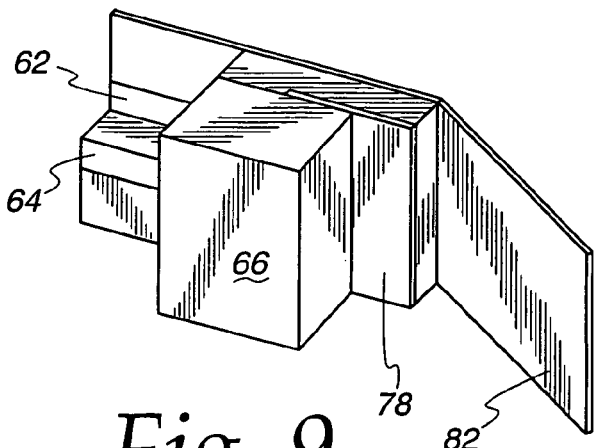
FIG. 8 is a perspective view of the assembly of an electro-chemical sensor according to one embodiment of the present invention.

Turning now to FIG. 8, the construction of a sensor 60 according to one embodiment of the present invention is more clearly shown. The spacer sheet 66 has been placed over a portion of the inner sensor sheet 64, leaving the inner electrode sample area 78 exposed. According to one embodiment of the present invention, the spacer sheet 66 is coated with adhesive on its sheet-contacting sides to enable the finished sensor 60 to adhere together. The outer sensor sheet 62 has been placed behind the inner sensor sheet 64. The outer sensor sheet 62 and the inner sensor sheet 64 may be adhered to each other by adhesive placed on the outer sensor sheet 62, the inner sensor sheet 64, or both. A distal portion 82 of the outer sensor sheet 62 is folded around a portion of the inner sensor sheet 64 and the spacer sheet 66 and adhered to the spacer sheet 66, thereby forming the sample fill area 68 as shown in FIG. 6. According to some embodiments of the present invention, the sensor 60 is adhered together with adhering methods other than or in addition to adhesives, such as UV cured epoxy.

Figure 9:
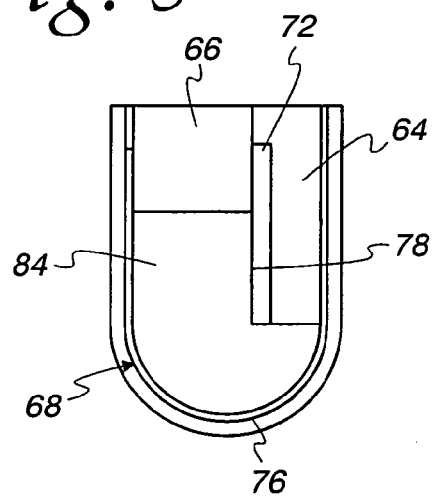
FIG. 9 is a cross-sectional view of the section defined by line 9-9 of FIG. 6.

Turning now to FIG. 9, a cross-section of the sensor 60 along the line 9-9 of FIG. 6 is shown. A sample 84 has been drawn into the sample fill area 68, for example by capillary action. The sample 84 contacts the outer electrode sample area 74 and the inner electrode sample area 78, enabling electro-chemical analysis of the sample. In the embodiment shown in FIG. 9, the spacer sheet 66 forms one boundary of the sample fill area 68.

Figure 10:
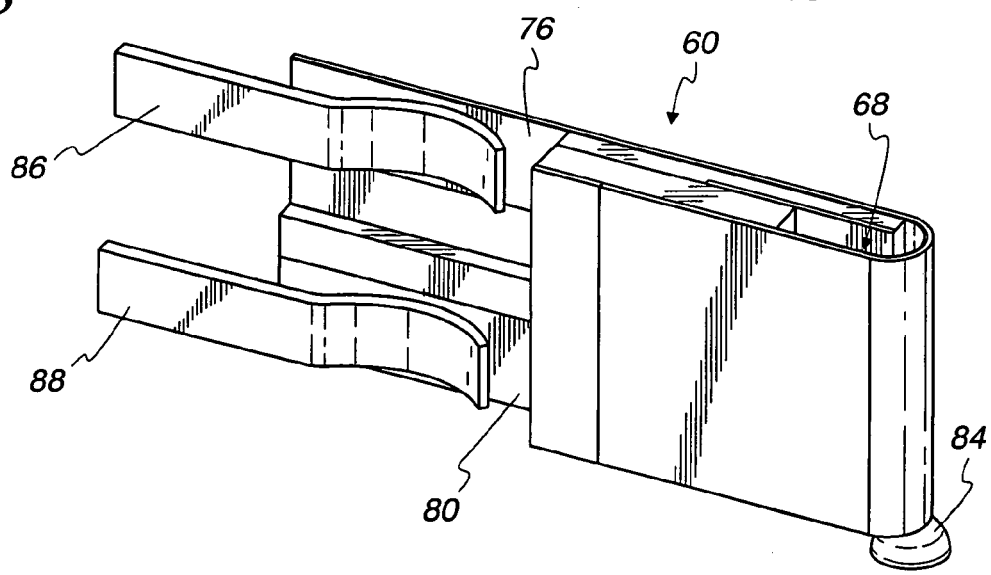
FIG. 10 is a perspective view of an electro-chemical sensor according to one embodiment of the present invention connected to an analysis instrument. While the invention is susceptible to various modifications and alternative forms, specific embodiments are shown by way of example in the drawings and will be described in detail herein. However, it should be understood that the invention is not intended to be limited to the particular forms disclosed. Rather, the invention is to cover all modifications, equivalents, and alternatives falling within the spirit and scope of the invention as defined by the appended claims.

Turning now to FIG. 10, a sensor 60 according to one embodiment of the present invention is shown in use. A sample 84 is being drawn into the sample fill area 68 by capillary action. Further, the sensor 60 is connected to an analysis instrument (not shown) by first and second instrument contacts 86 and 88. While the sensor 60 is shown being filled while connected to the analysis instrument, it is to be understood that the sensor 60 may be filled first and connected to an analysis instrument after filling. The instrument contacts 86 and 88 are connected, respectively, to the outer electrode contact area 76 and the inner electrode contact area 80. As discussed above, the outer electrode contact area 76 is in conductive contact with the outer electrode sample area 74 and the inner electrode contact area 80 is in conductive contact with the inner electrode sample area 78, thereby enabling electro-chemical analysis of the sample 84.

While the present invention has been described with reference to one or more particular embodiments, those skilled in the art will recognize that many changes may be made thereto without departing from the spirit and scope of the present invention. For example, while the present invention has been generally described as directed to medical applications it is to be understood that any optical fluid testing applications might employ the principles of the invention. Each of these embodiments and obvious variations thereof is contemplated as falling within the spirit and scope of the claimed invention, which is set forth in the following claims.

What is claimed is:

1. A sensor for electro-chemical analysis of a sample comprising:
   a top sheet having a top sample contact surface and a top sheet notch;
   a bottom sheet having a bottom sample contact surface and a bottom sheet notch;
   a spacer sheet between said top sheet and said bottom sheet and having first and second spacer sheet notches, said first spacer sheet notch aligning with said top sheet notch and said second spacer sheet notch aligning with said bottom sheet notch; and
   wherein said top sample contact surface and said bottom sample contact surface form a sample fill area for receiving said sample, and wherein greater than about 50% of a perimeter of said sample fill area is accessible to receive said sample, and
   wherein said top sample contact surface also extends from a body of said top sheet by a top neck and wherein said bottom sample contact surface extends from a body of said bottom sheet by a bottom neck, and further wherein a volume defined by said top sample contact surface and said bottom sample contact surface and having a height approximately equal to the width of said spacer sheet is adapted to contain said sample.

2. The sensor of claim 1 wherein said top sheet notch aligns with said first spacer sheet notch to expose a bottom sheet electrode on a top surface of said bottom sheet and said bottom sheet notch aligns with said second spacer sheet notch to expose a top sheet electrode on a bottom surface of said top sheet.

3. The sensor of claim 1 wherein said top sample contact surface is positioned above said bottom sample contact surface and spaced from said bottom sample contact surface by a separation distance approximately equal to the width of said spacer sheet.

4. The sensor of claim 3 wherein said separation distance is from approximately 0.0762 millimeter (0.003 inch) to approximately 0.254 millimeter (0.010 inch).

5. The sensor of claim 1 wherein at least one of said top sample contact surface and said bottom sample contact surface includes a surfactant and reagent.

6. The sensor of claim 1 wherein said top sample contact surface and said bottom sample contact surface includes a surfactant and reagent.

7. The sensor of claim 1 wherein both said top sample contact surface and said bottom sample contact surface are coated with a mixture of sample and reagent.

8. A sensor for the electro-chemical analysis of a sample comprising:
   an inner sensor sheet having first and second sides, an inner electrode area provided on at least a portion of said first side;
   a spacer sheet having first and second sides and connected along at least a portion of its first side to a portion of said first side of said inner sensor sheet; and
   an outer sensor sheet having an outer electrode area provided thereon and connected to at least a portion of said second side of said inner sensor sheet, said outer sensor sheet surrounding a portion of said inner sensor sheet and at least a portion of said spacer sheet and forming a sample fill area bounded by a portion of said outer sensor sheet, a portion of said inner sensor sheet, and a portion of said spacer sheet.

9. The sensor of claim 8 wherein said inner electrode area comprises
an inner electrode sample area and an inner electrode contact area, said inner electrode sample area being exposed to said sample fill area.

10. The sensor of claim 9 wherein said spacer sheet is adhesively connected to a distal portion of said outer sensor sheet and further adhesively connected to a portion of said inner electrode sheet so as to expose said inner electrode sample area.

11. The sensor of claim 8 wherein said outer electrode area comprises an outer electrode sample area and an outer electrode contact area, said outer electrode sample area being exposed to said sample fill area.

12. The sensor of claim 11 wherein said outer electrode sample area is an exposed portion of said outer electrode area bounded by said spacer sheet and said inner sensor sheet.

13. The sensor of claim 8 wherein said inner sensor sheet, said spacer sheet, and said outer sensor sheet are comprised of polycarbonate.

14. A sensor for electro-chemical analysis of a sample comprising:
a top sheet having a top sample contact surface;
a bottom sheet having a bottom sample contact surface;
a spacer sheet between said top sheet and said bottom sheet; and wherein only said top sample contact surface and said bottom sample contact surface form a sample fill area for receiving said sample, and wherein greater than about 50% of a perimeter of said sample fill area is accessible to receive said sample, and wherein said top sample contact surface extends from a body of said top sheet by a top neck and wherein said bottom sample contact surface extends from a body of said bottom sheet by a bottom neck, and further wherein a volume defined by said top sample contact surface and said bottom sample contact surface and having a height approximately equal to the width of said spacer sheet is adapted to contain said sample.

15. The sensor of claim 14 wherein said top sheet has a top sheet notch, said bottom sheet has a bottom sheet notch, and said spacer sheet has first and second spacer sheet notches, said first spacer sheet notch aligning with said top sheet notch to expose a bottom sheet electrode on a top surface of said bottom sheet, and said second spacer sheet notch aligning with said bottom sheet notch to expose a top sheet electrode on a bottom surface of said top sheet.

16. The sensor of claim 14 wherein at least one of said top sample contact surface and said bottom sample contact surface includes surfactant and reagent.

17. The sensor of claim 16 wherein said top sample contact surface and said bottom sample contact surface includes surfactant and reagent.

* * * * *